United States Patent
Yang

(10) Patent No.: US 11,772,133 B2
(45) Date of Patent: Oct. 3, 2023

(54) METHOD FOR REMOVING RESIDUAL ACID OF IMPLANT

(71) Applicant: Unidental Co., Ltd., Gwangmyeong-si (KR)

(72) Inventor: Sung Joon Yang, Yongin-si (KR)

(73) Assignee: UNIDENTAL CO., LTD., Gwangmyeong-si (KR)

( * ) Notice: Subject to any disclaimer, the term of this patent is extended or adjusted under 35 U.S.C. 154(b) by 0 days.

(21) Appl. No.: 17/573,644

(22) Filed: Jan. 12, 2022

(65) Prior Publication Data
US 2023/0020276 A1 Jan. 19, 2023

(30) Foreign Application Priority Data
Jul. 14, 2021 (KR) ........................ 10-2021-0092170

(51) Int. Cl.
*B08B 3/08* (2006.01)
*B08B 3/10* (2006.01)
*A61C 8/00* (2006.01)

(52) U.S. Cl.
CPC .............. *B08B 3/08* (2013.01); *A61C 8/0037* (2013.01); *B08B 3/10* (2013.01); *A61C 2008/0046* (2013.01)

(58) Field of Classification Search
None
See application file for complete search history.

(56) References Cited

U.S. PATENT DOCUMENTS

| | | | | |
|---|---|---|---|---|
| 5,876,453 A | * | 3/1999 | Beaty .................. | A61F 2/30767 433/201.1 |
| 2010/0218854 A1 | * | 9/2010 | Garcia Saban ........... | C23C 8/10 148/269 |

FOREIGN PATENT DOCUMENTS

KR  10-1311990 B1  9/2013

* cited by examiner

*Primary Examiner* — Eric W Golightly
*Assistant Examiner* — Arlyn I Rivera-Cordero
(74) *Attorney, Agent, or Firm* — Han's Law Office

(57) ABSTRACT

The present disclosure relates to a method for removing residual acid of implant that has been surface treated using acid, the method including thermal decomposition step of thermally decomposing and removing the acid remaining on the implant; base treatment step of treating the acid remaining on the implant with base, thereby neutralizing and removing the acid; and washing step of washing and removing the acid and the base remaining on the implant with washing water.

According to the present disclosure, the acid remaining on the surface of the fixture can be effectively removed, and thus there is an effect of preventing the problem of bone loss that may occur near the placed implant.

6 Claims, 3 Drawing Sheets

[Fig. 1]
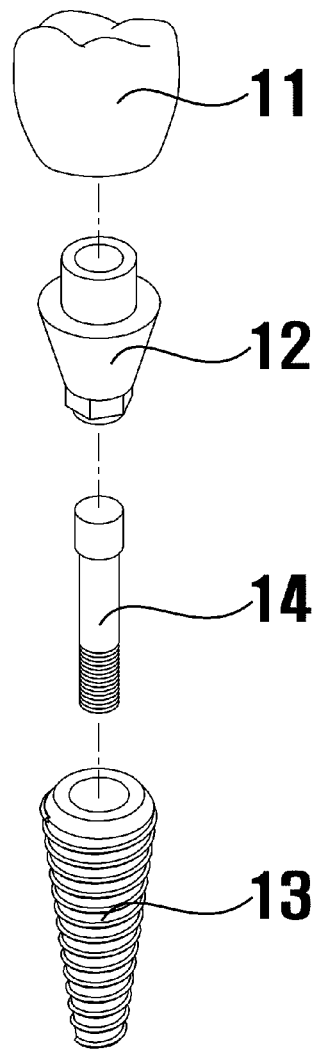
Related Art

[Fig. 2]
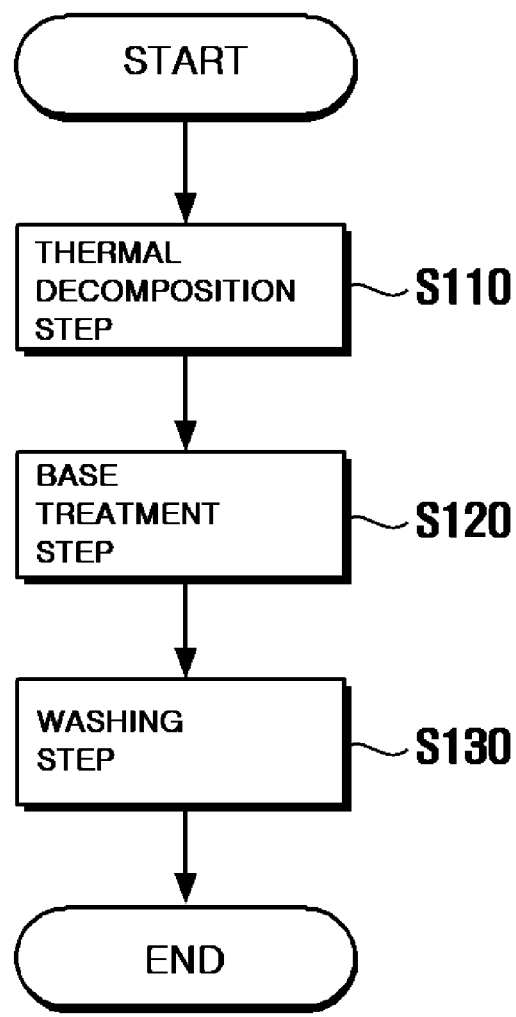

[Fig. 3]
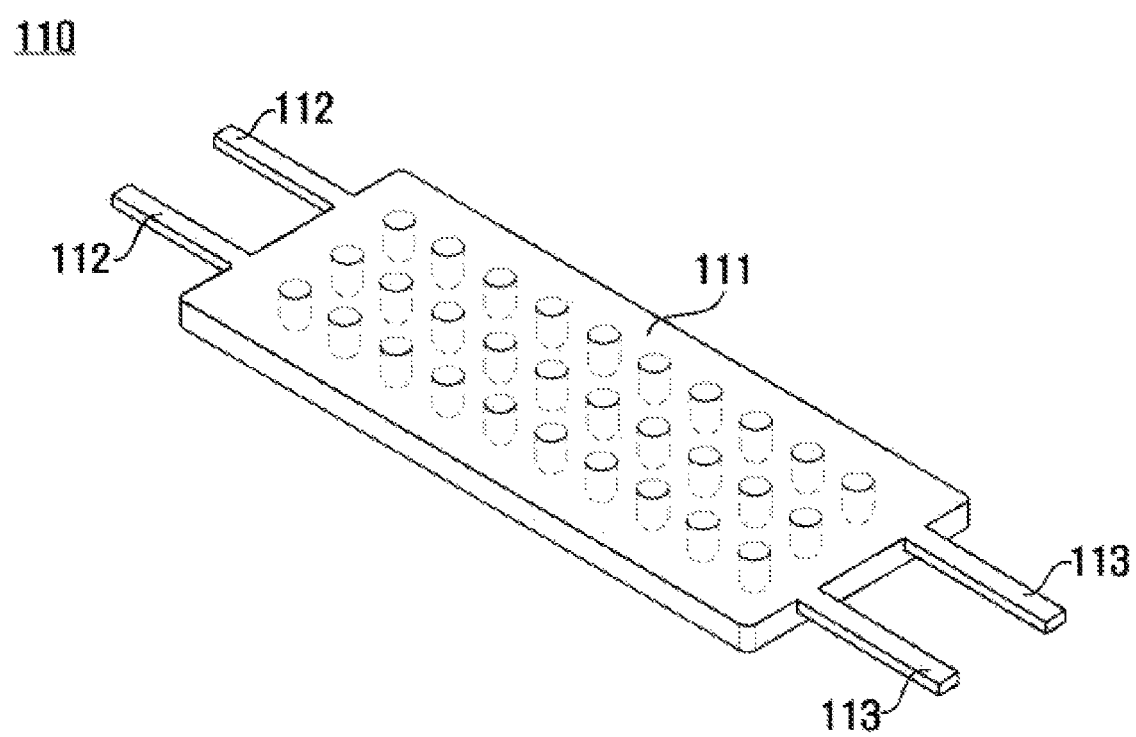

METHOD FOR REMOVING RESIDUAL ACID OF IMPLANT

1. FIELD

The present disclosure relates to a method for removing residual acid of implant, and more particularly, to a method for removing residual acid of implant, that is capable of effectively removing the acid remaining on a surface of an implant that has been surface treated.

2. BACKGROUND

A dental implant 10 is generally made by mechanically processing titanium or a titanium alloy, and then performing various surface treatment processes such as coating and the like.

As illustrated in FIG. 1, such a dental implant 10 is composed of a crown 11 that is formed to have an artificial tooth shape, an abutment 12 that may be coupled to a lower portion of the crown 11 and support the crown 11, a fixture 13 that may be placed in an alveolar bone and then the abutment 12 may be coupled to an upper portion of the fixture, thereby supporting the abutment 12, and a screw 14 that may be inserted inside the abutment 12 and the fixture 13, to firmly immobilize the abutment 12 and the fixture 13.

Meanwhile, of the components of the dental implant 10 described above, for the fixture 13, various surface treatment processes are performed to roughen its surface to improve intraosseous compatibility, such as the Sandblast Large grit Acid etch (SLA) surface treatment, Titanium Plasma Sprayed (TPS) surface treatment, Resorbable Blast Media (RBM) surface treatment and the like.

Of these surface treatment methods, the SLA surface treatment is a representative surface treatment method in which the body of the fixture 13 is carved as it is blasted with metal particles such as aluminum, and then acid corroded with strong acid. The surface of the fixture 13 is roughened by primarily being treated with sulfuric acid ($H_2SO_4$), and then secondarily with hydrochloric acid (HCl).

Here, there is a problem that, after the SLA surface treatment, the sulfuric acid and hydrochloric acid remain on the surface of the fixture 13, and if the implant is placed in the alveolar bone without completely removing the remaining sulfuric acid and hydrochloric acid, it may cause bone loss where the alveolar bone surrounding the implant melts, resulting in implant failure.

Therefore, in conventional methods, in order to remove the residual acid on the surface of the fixture 13, the surface of the fixture 13 used to be treated with a toxic strong base material such as sodium hydroxide (NaOH), and then the strong acid and strong base remaining on the surface of the fixture 13 used to be removed through at least 8 times of washing process.

However, such a conventional method has the disadvantage of lowering the overall production yield of the implant since it has to go through numerous washing processes. Further, there is also a problem that, despite the numerous washing processes, not only the strong acid but also the strong base that are harmful to human body could not be sufficiently removed from the surface of the fixture 13,

SUMMARY

A purpose of the present disclosure is to resolve the aforementioned problems of prior art, that is, to provide a method for removing residual acid of implant, that can effectively remove the acid remaining on the surface of the surface treated implant.

The aforementioned purpose can be achieved by a method for removing residual acid of implant that has been surface treated using acid, the method including thermal decomposition step of thermally decomposing and removing the acid remaining on the implant; base treatment step of treating the acid remaining on the implant with base, thereby neutralizing and removing the acid; and washing step of washing and removing the acid and the base remaining on the implant with washing water.

Further, the thermal decomposition step may be performed for 1 to 4 hours at 200° C. to 500° C.

Further, the base may be prepared as weak base.

Further, the weak base may be prepared as sodium bicarbonate aqueous solution.

Further, the washing step may be performed 3 to 5 times.

Further, the acid may include at least one of sulfuric acid and hydrochloric acid.

According to the present disclosure, since the residual acid on the surface of the fixture can be effectively removed, there is an effect of preventing the problem of bone loss that may occur around the placed implant.

Further, according to the present disclosure, since the number of times of the washing steps for washing the fixture can be significantly reduced, there is an effect of improving the overall production yield of implant.

Meanwhile, the effects of the present disclosure are not limited to the effects described above, and various effects may be included within the scope that is apparent to one skilled in the related art based on the description below.

BRIEF DESCRIPTION OF THE DRAWINGS

FIG. 1 is a view of the components of a dental implant;

FIG. 2 is a view of the total steps of the method for removing residual acid of implant according to one embodiment of the present disclosure; and FIG. 3 illustrates a tray on which a plurality of fixtures are mounted in thermal decomposition step of the method for removing residual acid of implant according to one embodiment of the present disclosure.

DETAILED DESCRIPTION

Hereinbelow, some embodiments of the present disclosure will be described in detail through illustrative drawings. It is to be noted that in adding reference numerals to the components of each drawing, the same components are given the same reference numerals as much as possible even though they are indicated on different drawings.

If it is determined that a detailed description of a related known configuration or function interferes with the understanding of the embodiment of the present disclosure, the detailed description thereof will be omitted.

Further, in describing the components of the embodiments of the present disclosure, terms such as first, second, A, B, (a), (b) and the like may be used. Such terms are used merely to distinguish those components from other components, and not to limit the essence, sequence or order and the like of the corresponding components.

Hereinafter, referring to the attached drawings, a method for removing residual acid of implant according to one embodiment of the present disclosure (S100) will be described in detail.

FIG. 2 illustrates the total steps of the method for removing residual acid of implant according to one embodiment of the present disclosure.

The present disclosure relates to a method for removing residual acid of implant that has been surface treated using acid (S100), and as illustrated in FIG. 2, the method for removing residual acid of implant according to one embodiment of the present disclosure (S100) includes thermal decomposition step (S110), base treatment step (S120) and washing step (S130).

The thermal decomposition step (S110) is a step of thermally decomposing the implant, that is, the sulfuric acid and hydrochloric acid remaining on the surface of the fixture 13 through sulfuric acid decomposition reaction and hydrochloric acid decomposition reaction. This step may be performed inside a tube furnace.

In more detail, the sulfuric acid decomposition reaction is a thermal decomposition reaction in which the sulfuric acid is decomposed into gaseous sulfur trioxide ($SO_3$) and water ($H_2O$) at a high temperature of 300° C. to 450° C. It is an endothermic reaction in which, as the sulfuric acid evaporates, it begins to decompose, and the higher the temperature, the better the reaction. The mechanism of the sulfuric acid decomposition reaction is as in the chemical formula 1 below.

$$H_2SO_4 \rightarrow SO_3(g) + H_2O(g) \quad \text{[Chemical Formula 1]}$$

The hydrochloric acid decomposition reaction is a thermal decomposition reaction in which the hydrochloric acid is decomposed into gaseous hydrogen ($H_2$) and chlorine ($Cl_2$) at a high temperature. It is an endothermic reaction in which the higher the temperature the better the reaction. The mechanism of the hydrochloric acid decomposition reaction is as in the chemical formula 2 below.

$$2HCl \rightarrow H_2(g) + Cl_2(g) \quad \text{[Chemical Formula 2]}$$

According to the sulfuric acid decomposition reaction and the hydrochloric acid decomposition reaction, at the thermal decomposition step (S110), the SLA surface treated fixture 13 may be inserted into the tube furnace, and then the thermal decomposition may be performed for 1 to 4 hours at a high temperature of 200° C. to 500° C., whereby the sulfuric acid and the hydrochloric acid remaining on the surface of the fixture 13 is thermally decomposed.

Here, there is a problem that if the temperature inside the tube furnace is below 200° C., the sulfuric acid decomposition reaction and the hydrochloric acid decomposition reaction do not occur sufficiently, and if the temperature inside the tube furnace is 500° C. or above, after the sulfur trioxide ($SO_3$) is decomposed into sulfur dioxide ($SO_2$) and oxygen ($O_2$), due to the decomposed oxygen gas, titanium will be oxidized, thus forming a titanium dioxide ($TiO_2$) film on the surface of the fixture 13.

$$H_2O + SO_3 \rightarrow SO_2(g) + H_2O(g) + \frac{1}{2}O_2(g) \quad \text{[Chemical Formula 3]}$$

Further, the atmosphere in the tube furnace may be prepared as a hydrogen atmosphere. It may be prepared such that gases such as sulfur trioxide, chlorine and the like that have been thermally decomposed can flow naturally through the hydrogen gas flowing in the tube furnace.

Meanwhile, the atmosphere in the tube furnace may be prepared as an argon atmosphere or a hydrogen-argon mixed atmosphere.

As described above, additionally, there is also a problem that at a high temperature near 500° C. or above, the sulfur trioxide may be decomposed into sulfur dioxide and oxygen, wherein due to the generated oxygen gas, titanium may be oxidized, forming a titanium oxide film on the surface of the fixture 13, and as a result, the commodity value of the fixture 13 will be significantly degraded.

Accordingly, in the present disclosure, in order to prevent the titanium being oxidized and thus to prevent the titanium oxide film being formed on the surface of the fixture 13, the atmosphere in the tube furnace may be prepared an argon atmosphere that is inert to oxygen or a hydrogen-argon mixed atmosphere.

According to the thermal decomposition step (S110) as described above, there is an effect of effectively removing the sulfuric acid and the hydrochloric acid on the surface of the fixture 13, and also preventing the titanium oxide film being formed on the surface of the fixture 13.

Meanwhile, the tube furnace at the thermal decomposition step (S110) may include a tray 110 onto which a plurality of fixtures 13 may be mounted. That is, the plurality of fixtures 13 that have been surface treated using acid may be inserted into the tube furnace after being mounted onto the tray 110 when being inserted into the tube furnace. It is desirable that such a tray 110 is made of titanium alloy so as to withstand the high temperature in the tube furnace.

Meanwhile, if the tray 110 is in direct contact with an inner circumferential surface of the tube furnace, there is a problem that the tube furnace may be damaged at a high temperature. Accordingly, as illustrated in FIG. 3, in the present disclosure, the tray 110 includes a main part 111, a first insertion part 112 and a second insertion part 113.

The main part 111 is where the plurality of fixtures 13 may be mounted onto. The main part 111 is prepared in a thin plate form, and has a plurality of penetration holes.

The first insertion part 112 is formed to extend from one side of the main part 111 in a longitudinal direction, and is inserted into a first insertion groove formed in a cover at one side of the tube furnace.

The second insertion part 113 is formed to extend from the other side of the main part 111 in the longitudinal direction, and is inserted into a second insertion groove formed in a cover at the other side of the tube furnace.

That is, in the cover at one side of the tube furnace and in the cover at the other side of the tube furnace, the first insertion groove and the second insertion groove into which the first insertion part 112 and the second insertion part 113 may be inserted are formed respectively. When placing the tray 110 into the tube furnace after mounting the plurality of fixtures onto the tray 110, if the first insertion part 112 can be inserted into the first insertion groove formed in the cover at one side of the tube furnace and then immobilized, and then the second insertion part 113 can be inserted into the second insertion groove and then immobilized when closing the cover at the other side, it is possible to have the tray 110 be stably immobilized inside the tube furnace and at the same time have the tray 110 not directly contact the inner circumferential surface of the tube furnace.

Meanwhile, the first insertion part 112 and the second insertion part 113 may be formed in plural number so that the tray 110 can be stably immobilized inside the tube furnace, and it is desirable that the cross-sectional shape of the first insertion part 112, the second insertion part 113, the first insertion groove and the second insertion groove are formed in a polygonal shape such as a quadrangle.

According to the tray 110 as described above, there is an effect that a plurality of fixtures 13 can be stably mounted inside the tube furnace, and that the tube furnace can be prevented from being damaged by the high temperature tray 110.

The base treatment step (S120) is a step of treating the acid remaining on the surface of the fixture 13 with base, thereby neutralizing and removing the acid. It is a step of neutralizing with weak base the remaining sulfuric acid and hydrochloric acid that were not thermally decomposed at the thermal decomposition step (S110) described above, and thus removing the same.

In conventional methods, in order to remove the residual acid on the surface of the fixture 13, it was treated with a toxic strong base such as sodium hydroxide (NaOH). However, according to such a method, the strong base may remain on the surface of the fixture 13 even after several washing steps (S130), and thus there was a problem of being harmful to human body.

Accordingly, in the present disclosure, primarily, at the thermal decomposition step (S110), the residual sulfuric acid and hydrochloric acid are thermally decomposed and mostly removed, and then secondarily, at the base treatment step (S120), the residual acid is treated with the weak base that is harmless to human body, thus neutralizing and removing the small amount of residual sulfuric acid and hydrochloric acid that were not thermally decomposed at the thermal decomposition step (S110).

Here, the weak base at the base treatment step (S120) is a representative weak base, and can be prepared as an aqueous solution of sodium bicarbonate ($NaHCO_3$), which is widely known to be harmless to human body.

According to the base treatment step (S120) as described above, there is an advantage that the small amount of residual sulfuric acid and hydrochloric acid that were not thermally decomposed at the thermal decomposition step (S110) can be neutralized and removed, and even if there is weak base that couldn't participate in the neutralizing reaction remaining on the surface of the fixture 13, it is harmless to human body.

The washing step (S130) is a step of washing and removing the acid and base that could not participate in the neutralizing reaction and remains on the surface of the fixture 13 with washing water. Here, the washing water may be prepared as distilled water ($H_2O(l)$).

Conventional methods had to go through at least 8 washing processes to remove the sulfuric acid and hydrochloric acid, which are strong acids, and sodium hydroxide, which is a strong base. However, this would deteriorate the overall implant production yield due to the numerous washing processes, and there was also a disadvantage that the strong acid and strong base cannot be sufficiently removed since the strong acid and strong base are removed by only washing water.

However, in the present disclosure, the sulfuric acid and hydrochloric acid can be sufficiently removed at the thermal decomposition step (S110) described above, and the acid is removed by treating with the weak base that is harmless to human body at the base treatment step (S120), and thus the acid and base may be removed through a smaller number of washing processes.

Accordingly, the washing step (S130) of the present disclosure may be performed repeatedly 3 to 5 times, or desirably 4 times.

According to the washing step (S130) as described above, since the number of times of the washing step (S130) for washing the fixture 13 may be significantly reduced, there is an effect of improving the overall production yield of implant.

According to the method for removing residual acid of implant according to one embodiment of the present disclosure (S100) that includes the thermal decomposition step (S110), the base treatment step (S120) and the washing step (S130) as described above, the acid remaining on the surface of the fixture 13 can be effectively removed, and thus there is an effect of preventing the problem of bone loss that may occur near the placed implant.

Further, according to the present disclosure, there is an effect that the number of times of the washing step (S130) for washing the fixture 13 may be significantly reduced, thereby improving the overall production yield of implant.

Hereinbelow, the operation and effect of the present disclosure will be described in more detail through specific embodiments of the present disclosure. However, these are presented as examples of the present disclosure, whereby the scope of the present disclosure is not limited in any sense.

Example—Fixture where the Method for Removing Residual Acid of the Present Disclosure is Applied By applying the method for removing residual acid of implant according to one embodiment of the present disclosure, the fixture 13 was tested in the following manner.

The fixture 13 of a dental implant 10 for SLA surface treatment was placed in a hydrogen atmosphere tube furnace, and then thermally decomposed for 2 hours under a 200° C. condition to remove the sulfuric acid and hydrochloric acid on the surface of the fixture 13, and then the fixture 13 was withdrawn from the tube furnace, and the surface of the fixture 13 was neutralized with a 3% sodium hydroxide aqueous solution. Then, the fixture 13 was washed 4 times with distilled water.

Experiment Example—pH Measurement/Eluate Test pH measurement was conducted through an eluate test. It was prepared by pretreating under a condition of 4 g/20 mL/50° C. for 72 hours, thereby eluting a test solution. pH measurement was conducted according to the pH section in the Korean Pharmacopoeia General Test Method, and S220-BIO model of Mettler was used as the pH meter to measure the pH of the eluted test solution.

As a result of measurement by the above method, the pH of the fixtures 13 to which the method for removing residual acid of the present disclosure was applied were 6.48 and 6.68, showing that the residual sulfuric acid and hydrochloric acid on the surface of the fixture 13 were effectively removed.

In the above, even though it was described that all components constituting the embodiment of the present disclosure are combined or operate in combination, the present disclosure is not necessarily limited to this embodiment. That is, within the scope of the present disclosure, one or more of all the components may be selectively combined and operate.

Further, terms such as "include/comprise", "constitute" or "have/has" described above mean that the corresponding components may be inherent, unless otherwise state, and thus it should be interpreted that other components may be further included, instead of excluding the other components. All terms, including technical or scientific terms, have the same meaning as commonly understood by one of ordinary skill in the art to which the present disclosure belongs, unless otherwise defined. Terms commonly used, such as those defined in the dictionary, should be interpreted as being consistent with the contextual meaning of the related art, and unless explicitly defined in the present disclosure, they should not be interpreted in an ideal or excessively formal meaning.

In addition, the above description is merely illustrative of the technical idea of the present disclosure, and those of ordinary skill in the art to which the present disclosure pertains may make various modifications and variations without departing from the essential characteristics of the present disclosure.

Therefore, the embodiments disclosed in the present disclosure are not intended to limit the technical spirit of the present disclosure, but to explain, and the scope of the technical spirit of the present disclosure is not limited by these embodiments. The protection scope of the present disclosure should be construed by the following claims, and all technical ideas within the scope equivalent thereto should be construed as being included in the scope of the present disclosure.

What is claimed is:

1. A method for removing residual acid of an implant that has been surface treated using acid, the method comprising:

thermal decomposition step of thermally decomposing and removing the acid remaining on a surface of the implant in a tube furnace;

after the thermal decomposition step, base treatment step of treating the acid remaining on the surface of the implant with a base, thereby neutralizing and removing the acid; and after the base treatment step, washing step of washing and removing the acid and the base remaining on the surface of the implant with washing water, wherein the thermal decomposition step is performed at an argon atmosphere or a hydrogen-argon mixed atmosphere in the tube furnace.

2. The method for removing residual acid of an implant according to claim 1, wherein the thermal decomposition step is performed for 1 to 4 hours at 200° C. to 500° C.

3. The method for removing residual acid of an implant according to claim 1, wherein the washing step is performed 3 to 5 times.

4. The method for removing residual acid of an implant according to claim 1, wherein the acid comprises at least one of sulfuric acid and hydrochloric acid.

5. The method for removing residual acid of an implant according to claim 1, wherein the base is prepared as weak base.

6. The method for removing residual acid of an implant according to claim 5, wherein the weak base is prepared as sodium bicarbonate aqueous solution.

* * * * *